US00RE44896E

(19) United States
(12) Reissued Patent
Cha

(10) Patent Number: US RE44,896 E
(45) Date of Reissued Patent: May 13, 2014

(54) DISSECTING HIGH SPEED BURR FOR SPINAL SURGERY

(71) Applicant: Charles W. Cha, Marietta, GA (US)

(72) Inventor: Charles W. Cha, Marietta, GA (US)

(73) Assignee: Spinascope, Inc., Cartersville, GA (US)

(21) Appl. No.: 13/873,360

(22) Filed: Apr. 30, 2013

Related U.S. Patent Documents

Reissue of:

(64) Patent No.: 7,585,300
Issued: Sep. 8, 2009
Appl. No.: 11/017,150
Filed: Dec. 20, 2004

U.S. Applications:

(60) Provisional application No. 60/531,209, filed on Dec. 19, 2003.

(51) Int. Cl.
*A61B 17/32* (2006.01)

(52) U.S. Cl.
USPC ..... 606/80

(58) Field of Classification Search
USPC ..... 606/79, 80, 84, 85, 159, 167, 170, 180; 433/116; 451/451
See application file for complete search history.

(56) References Cited

U.S. PATENT DOCUMENTS

| | | | |
|---|---|---|---|
| 2,429,356 | A | 1/1947 | Hicks |
| 4,541,423 | A | 9/1985 | Barber |
| 5,138,797 | A | 8/1992 | Siden |
| 5,411,514 | A | 5/1995 | Fucci et al. |
| 5,620,447 | A | 4/1997 | Smith et al. |
| 5,851,208 | A | 12/1998 | Trott |
| 5,851,212 | A | 12/1998 | Zirps et al. |
| 5,938,678 | A | 8/1999 | Zirps et al. |
| 6,053,907 | A | 4/2000 | Zirps |
| 6,077,287 | A | 6/2000 | Taylor et al. |
| 6,464,711 | B1 | 10/2002 | Emans et al. |
| RE38,335 | E | 11/2003 | Aust et al. |
| 6,645,218 | B1 | 11/2003 | Cassidy et al. |
| 6,656,195 | B2 | 12/2003 | Peters et al. |
| 7,785,337 | B2 | 8/2010 | Adams et al. |
| 8,277,474 | B2 | 10/2012 | Norman et al. |

*Primary Examiner* — Pedro Philogene
*Assistant Examiner* — David Comstock
(74) *Attorney, Agent, or Firm* — Duane Morris LLP

(57) ABSTRACT

A rotatable surgical burr (100, 200, 300, 500) having a protective hood (120, 220, 320, 520, 620, 720) with a dissecting foot plate (119, 219, 319, 519, 619, 719) is provided to improve and enable various spinal decompression procedures. The surgical burr's protective hood has a dissecting foot plate that may be shaped to resemble a curette, a Woodson, or other appropriate dissecting tools to allow insertion of the tool between the spinal nerve and the compressing bone. The protective hood surrounds the burr bit (130, 230, 530) exposing only a portion of the burr bit for burring of the offending bone and protects the nerve from the burr tip. The instrument may also be configured with a soft tissue resecting tip (330) for soft tissue resection.

13 Claims, 18 Drawing Sheets

DISSECTING HIGH SPEED BURR FOR SPINAL SURGERY

Matter enclosed in heavy brackets [ ] appears in the original patent but forms no part of this reissue specification; matter printed in italics indicates the additions made by reissue.

CROSS-REFERENCE TO RELATED APPLICATIONS

This application claims the benefit of U.S. Provisional Application No. 60/531,209 filed on Dec. 19, 2003, the contents of which is incorporated herein by reference.

FIELD OF THE INVENTION

This invention relates to a surgical instrument and more particularly to a surgical high-speed burr for use in spinal surgical procedures.

BACKGROUND OF THE INVENTION

Spinal stenosis is a degenerative condition of the spine that afflicts primarily the elderly population. Patients with lumbar spinal stenosis suffer from severe radiating pain, which limits their ability to ambulate and can cause weakness and numbness in the legs and in severe cases, loss of bowel and bladder control may occur. It is the development of hypertrophic bone spurs off the facet joints, protrusions of the disc annulus, as well as hypertrophy of the ligamentum flavum that combine to narrow the space available for the nerves in the spinal canal.

The standard surgical procedure to treat lumbar spinal stenosis is known as the lumbar laminectomy and foraminotomy. During this procedure, the surgeon removes the spinous processes, the interspinous ligaments and the central portion of the spinal lamina to gain a line of sight into the lateral recess and into the foramen so that the nerve compression can be relieved in these areas. The current standard tools for performing this procedure are the Kerrison punch and angled curettes and in severe instances, osteotomes. To remove the offending bone using these instruments, a surgeon places the instrument into the interval between the compressing bone and the underlying nerve that is being compressed and the bone is then removed from the dorsal aspect of the nerve where it is impinged, thereby relieving compression exerted on the spinal nerve. In situations where the compression on the nerve is not very severe, one can safely insert the Kerrison footplate or the curette into the interval between the nerve root and the surrounding bone to perform the necessary bone removal.

However, when there is a severe amount of compression at the neural foramen or the lateral recess, the interval between the nerve root and the encroaching bone may not be sufficient to safely conduct the neural decompression using the conventional tools, such as a Kerrison punch or a curette. Insertion of a Kerrison footplate or a curette into a severely stenotic interval may cause compressive injury to an already compressed nerve root. In these situations, the only conventionally available method of successfully decompressing the neural compression, especially in the foramen, has been to pass a small curved osteotome in the plane that is superior to the nerve root and osteotomize the bone that is encroaching on the nerve root from above. This maneuver, however, poses risk to the nerve root because there is a possibility that the osteotome will slip or advance too deep, thereby damaging the exiting nerve. Thus, there is a need for an improved instrument that would allow a safer, more controlled method of foraminal lateral recess decompression that minimizes risks to the nerve roots, especially in severely stenotic situations.

Additionally, the need to remove the interspinous ligament, the spinous processes and the central portion of the lamina in open lumbar laminectomy is only to allow the surgeon to have a line of sight into the lateral recess and foramen to remove pressure on the compressed nerve. In surgery, the surgeon works from the opposite side of the table to get the appropriate line of sight and angle of attack at the encroaching bone and soft tissue in the lateral recess in the foramen. Working from the contralateral side of the table is necessary in order to be able to undercut the facet joints and thereby preserve spinal stability with these procedures. This line of attack is necessary because of the shape of the current standard instruments, such as a Kerrison punch, curette or osteotome, and the necessary vector of applied force that is required using those instruments. There is therefore an additional need for an instrument that would allow for ipsilateral decompression of the lateral recess and the foramen. This instrument would need to allow for undercutting of the facet joints and removal of compressive bone and soft tissue in the lateral recess and the foramen on the ipsilateral side of the patient (decompression on the same side of the table as opposed to working across the spinal canal from the contralateral side of the table). Such an instrument would also allow for the application of minimally invasive techniques to perform lumbar decompressions and would allow for the maximal preservation of bone and ligaments thereby preserving spinal stability.

One tool that is available to a spine surgeon to remove bone, in a controlled fashion, is a high speed burr. The burr is used from the dorsal surface of the bone heading towards the neural elements and the bone is thinned down until it is wafer thin and can be picked away with curettes. If one is too aggressive with the burr, then neural injury can occur by penetrating the dura or wrapping the neural elements in the burr bit. Because the risk of catching the neural elements with the conventional high speed burr bit is too high, the use of conventional high speed burrs to perform the lateral recess and foraminal decompression has not been practicable. Thus, an improved novel high speed burr for removing bone in such tight spaces is desired.

SUMMARY

A surgical instrument according to an embodiment of the invention comprises a hand piece, a rigid shaft portion extending from the hand piece and having a distal end and a proximal end, and a drive shaft disposed for rotation within the shaft portion. The drive shaft has a distal end and a proximal end thereof and a surgical tool bit is connected to the distal end of the drive shaft. A protective hood including a dissecting foot plate portion is connected to the distal end of the shaft portion. And the surgical tool bit resides within the protective hood, partially exposed, and the protective hood is rotatable relative to the surgical tool bit along the longitudinal axis of the surgical tool bit, exposing a different portion of the surgical tool bit.

A surgical instrument according to another embodiment comprises a hand piece, a power drive mechanism provided within the hand piece, a rigid shaft portion extending from the hand piece and having a distal end and a proximal end, and a drive shaft disposed for rotation within the shaft portion. The drive shaft has a distal end and a proximal end thereof, and the proximal end is connected to the power drive mechanism. A surgical tool bit is connected to the distal end of the drive shaft and a protective hood including a dissecting foot plate portion is attached to the distal end of the shaft portion. The surgical tool bit resides within the protective hood, partially exposed, and the protective hood is rotatable relative to the surgical tool bit along the longitudinal axis of the tool bit, exposing a different portion of the surgical tool bit.

The dissecting soft tissue resector embodiment could also be used, with an extended kind of a Woodson type tip, to get in between compressive tissue and the nerve root that is sometimes found in the foramen that can continue to cause residual compression on the nerve, even after a dorsal bony decompression has been performed. The dissecting soft tissue resector may be used to debride annulus, ligamentum flavum, disc and or cartilage that are encroaching the nerve root in the axilla or in the foramen.

In addition to allowing a safer foraminal decompression in the open setting, the dissecting burr according to an embodiment of the invention is also suited for performing lumbar decompression in minimally invasive surgical settings while sparing bone and ligament that are in close proximity to the surgical site.

BRIEF DESCRIPTION OF THE DRAWING

The drawings are schematic and the like reference numerals used in the figures denote like parts throughout the various figures.

FIG. 1b is a detailed side elevational view of region A in FIG. 1a.

FIG. 1c is a front elevational view of the region A in FIG. 1a.

FIG. 2b is a front elevational view of the dissecting burr of FIG. 2a.

FIG. 3b is a front elevational view of the dissecting soft tissue resector of FIG. 3a.

FIG. 4b is a cross-sectional schematic illustration of the inner shaft member of FIG. 4a;

FIG. 5c is a cross-sectional schematic illustration of region B in FIG. 5a.

DETAILED DESCRIPTION

Figure 1A:
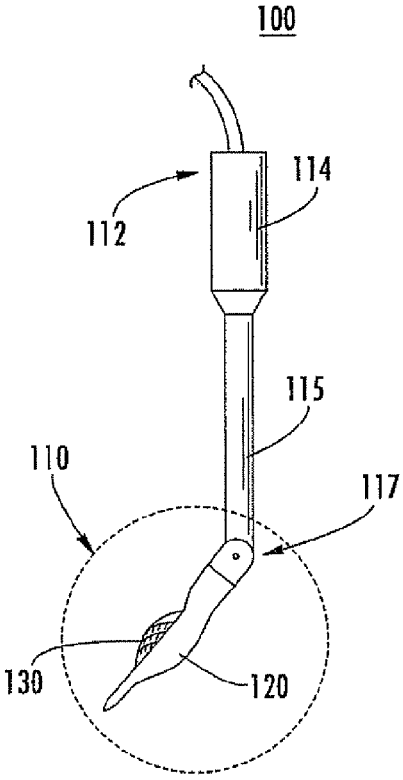
FIG. 1a is a side elevational view of a dissecting burr according to an embodiment of the invention.

Various embodiments of the dissecting high speed burr according to the invention will now be described in reference to the FIGS. 1 through 5. The embodiments illustrated in these drawings are presented as examples of various embodiments of the invention only. These illustrations are not meant to limit the invention to these examples. The illustrations are not to scale and, thus, the relative dimensions of some of the aspects of the instrument may be exaggerated.

Referring to FIGS. 1a-1d, a dissecting burr 100 according to an embodiment of the invention is disclosed. The dissecting burr 100 comprises a hand piece 114 at its proximal end 112 and a bone burring surgical tool bit, a burr bit 130, at its distal end 110 housed in a protective hood 120. A generally hollow outer tube 115 connects the hand piece 114 to the protective hood 120.

In an embodiment of the invention, the outer tube 115 may be angled at a region 117 near the distal end 110 to allow the instrument to reach into the neural foramen of a patient during a foraminal decompression. The angled region 117 may be configured and adapted to have a fixed angle or provided with a hinged or other articulated flexible joints to allow the angle of the distal end 110 of the instrument to be adjusted as desired.

In another embodiment, the outer tube 115 may be straight without any angled neck portion 117. Such straight burr instrument may not be suitable for foraminal decompression but could be used in situations where the bone spurs are encroaching the foramen from the posterior lip of the ventral vertebral bodies. The straight dissecting burr may be used to go in underneath a nerve root and remove the ventrally encroaching bone. Currently, there are no tools that allow for the safe removal of bone ventral to the nerve root in the foramen.

The hand piece 114 functions as a handle for the surgeon to hold and manipulate the dissecting burr 100 and may house a power drive mechanism, such as an electrical motor or a pneumatic drive mechanism, to drive the burr bit 130 of the dissecting burr 100. The burr bit 130 also may be driven by other suitable driving means. An elongated outer tube 115 connects the hand piece 114 and the protective hood 120. The outer tube 115 houses an appropriate mechanical linkage that connects the power drive mechanism to the burr bit 130.

The protective housing 120 has an opening 122 exposing one portion of the burr bit 130. Generally, the superior or dorsally facing surface of the burr bit 130 is exposed while the undersurface of the burr bit 130 is protected by a protective hood 120. The protective hood 120 includes a dissecting foot plate portion 119, the portion of the protective hood 120 from about the widest portion to the distal tip 118, that is shaped to enable the distal end 110 of the dissecting burr 100 to be inserted between the encroaching bone and the nerve root during a foraminal decompression procedure, for example. The protective hood 120 enshrouding the burr bit 130 protects the surrounding soft tissue, such as the nerve root, from being damaged by the burr bit 130 during the bone burring procedure.

The dissecting footplate 119 is shaped like a surgical dissection tool such as a curette, the Woodson, etc. During surgery, the distal end 110 of the dissecting burr 100 is placed in the neural foramen with the exposed burr bit 130 oriented towards the offending bone. The rest of the burr bit 130 is covered by the protective hood 120, which rests against the underlying nerve root thereby protecting the nerve from the burr bit 130.

Figure 1B:
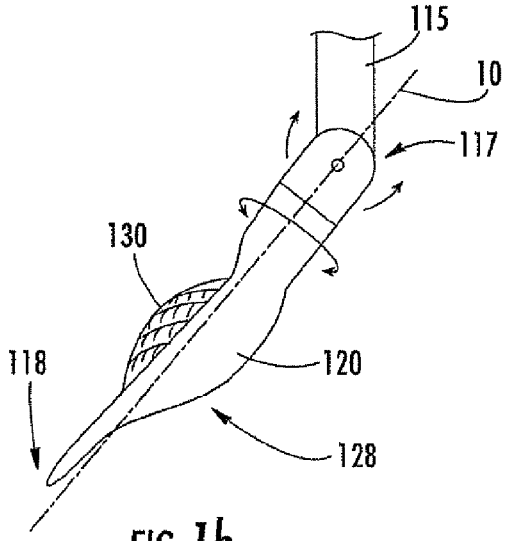
Figure 1C:
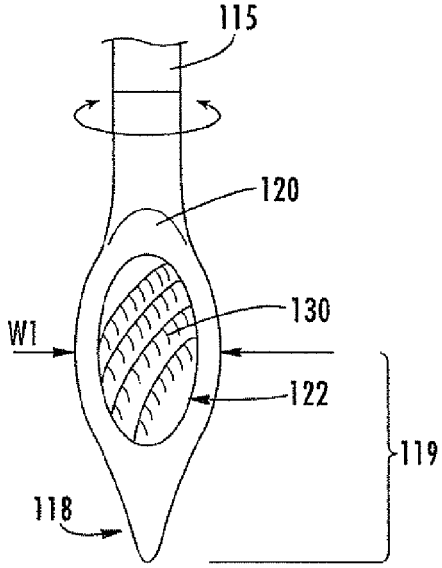

FIGS. 1b and 1c are detailed side view and a frontal view, respectively, of the distal end 110 of the dissecting burr 100. The protective hood 120 may be axially rotatably attached to the outer tube 115 so that the protective hood 120 is rotatable about a longitudinal axis 10 of the distal end 110 of the dissecting burr 100. The opening 122 of the protective hood 120 is sized and configured to expose a desired amount of the burr bit 130 appropriate for the bone removal to be performed with the instrument. By having an axially rotatable protective hood 120, the burr bit's exposed cutting portion can be repositioned to accommodate to the varying geometric relationship of the offending bone to the compressed nerve. In other words, the protective hood 120 may be axially rotated, changing the angle of attack of the burr bit 130. The dissecting burr 100 is mechanically configured such that the rotational motion of the protective hood 120 is manipulable by the surgeon from the hand piece 114. Thus, the surgeon can change the direction of the bone resection without moving the whole instrument, the dissecting burr 100, just by manipulating the orientation of the protective hood 120 from the hand piece 114.

Conversely, the protective hood 120 is positioned to maximally protect the underlying nerve from the exposed burr face. This configuration allows the angular orientation of the opening 122 in the protective hood 120 to be changed about its longitudinal axis and change the direction of the exposed burr bit.

Figure 1D:
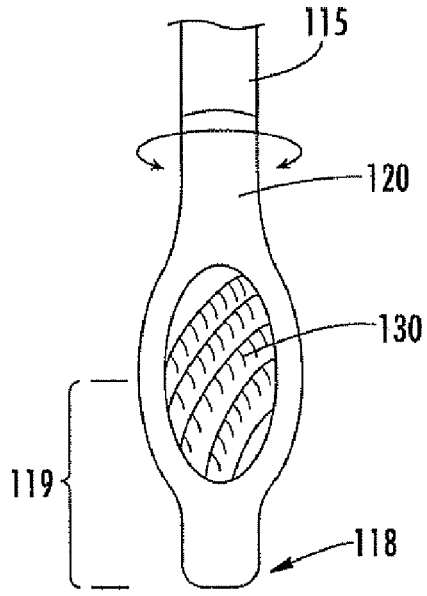
FIG. 1d is a front elevational view of the dissecting burr of FIG. 1c with an alternative shape for the dissecting foot plate according to another embodiment of the invention.
Figure 1E:
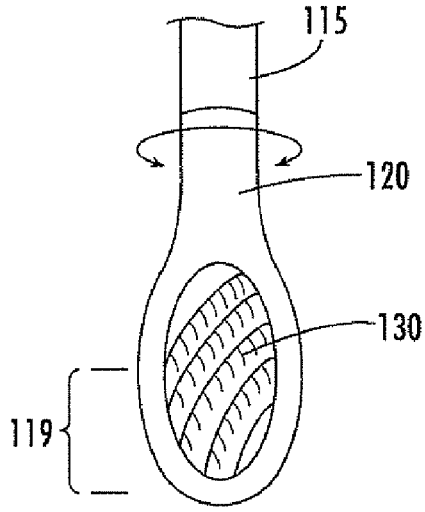
FIG. 1e is an illustration of a dissecting foot plate of a dissecting burr according to another embodiment.

The burr bit 130, the protective hood 120 and the dissecting foot plate portion 119 of the dissecting burr 100 may be made in any desired sizes. In one embodiment, the protective hood 120 and the dissecting foot plate portion 119 may be provided in the following dimensions that are useful for foraminal decompression. In this example, the dissecting foot plate 119 of the instrument is illustrated with a shape resembling a Woodson tip. In FIGS. 1c and 1d, a dissecting burr instrument having Woodson-type dissecting foot plate 119 according to an embodiment of the invention is disclosed. In FIG. 1e, a dissecting burr instrument having a curette-type dissecting foot plate 119 according to another embodiment is disclosed.

TABLE

| Burr Bit Diameter | 2 mm | | 3 mm | | 4 mm | |
|---|---|---|---|---|---|---|
| Protective Hood Size (diameter at the widest portion) | 3 mm | 8 mm | 4 mm | 9 mm | 5 mm | 10 mm |
| Dissecting Foot Plate Size | 1 to 8 mm long with taper depending on the width of the protective hood. | | | | | |

The protective hood sizes are the diameter W1 (FIG. 1c) of the hood measured at the widest portion. In these examples, there are two sizes of protective hood 120 for each burr bit size. The larger diameter protective hoods are primarily intended for central laminectomy whereas the smaller protective hoods are primarily intended for foraminotomy. This preference is determined by the amount of protection needed for the nerve tissue depending on the type of procedure and the location in which the instrument is being used to remove bony tissues from the patient. Some procedures require more protection from the burr for the other tissues surrounding the surgical site.

During surgery, the surgeon inserts the dissecting foot plate portion 119 of the dissecting burr 100 into the interval between the nerve root and the overlying compressing bone and continue to insert the instrument into the interval until the burr is positioned at a suitable location for removing the encroaching bone. The dissecting burr 100 is then turned on at high speed and the burr bit 130 is generally pushed forward into the encroaching bone. As such the whole width of the dissecting burr 100 is not forced into the interval between the bone and the nerve root. This minimizes any additional compression that may be exerted by the dissecting burr 100 because as the burr is advanced, the overlying bone is resected. The amount of bone that is removed depends on the combined girth or the diameter of the burr bit 130 and the protective hood 120 that is inserted into the interval.

Figure 2A:
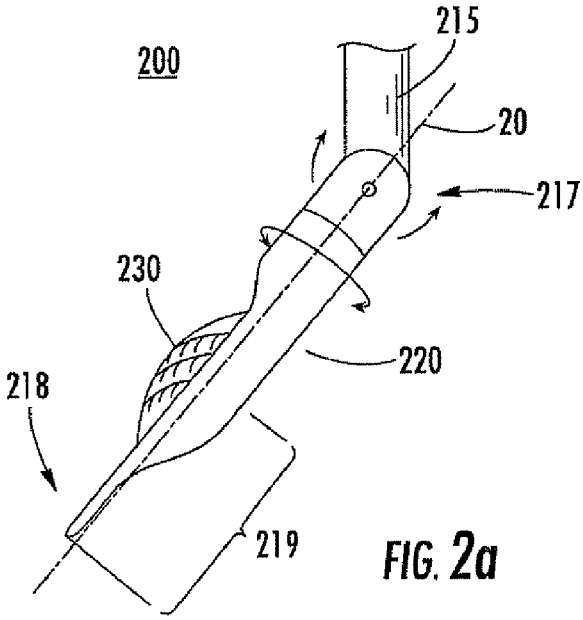
FIG. 2a is a side elevational view of the distal end of another dissecting burr according to another embodiment of the invention.

FIG. 2a is a schematic side view illustration of a dissecting burr 200 according to another embodiment of the invention. The dissecting burr 200 of this embodiment is similar to that illustrated in FIGS. 1a-1c. The dissecting burr 200 comprises an axially rotatable protective hood 220 that houses a burr bit 230. The protective hood 220 is axially rotatably attached to outer tube 215. The diameter of the outer tube 215 and the diameter of the rotating protective hood 220 are substantially similar throughout their lengths without the bulged portion 128 of the protective hood 120 in the embodiment of the dissecting burr 100. Such configuration provides smoother profile that may be beneficial during a surgical procedure.

Figure 2B:
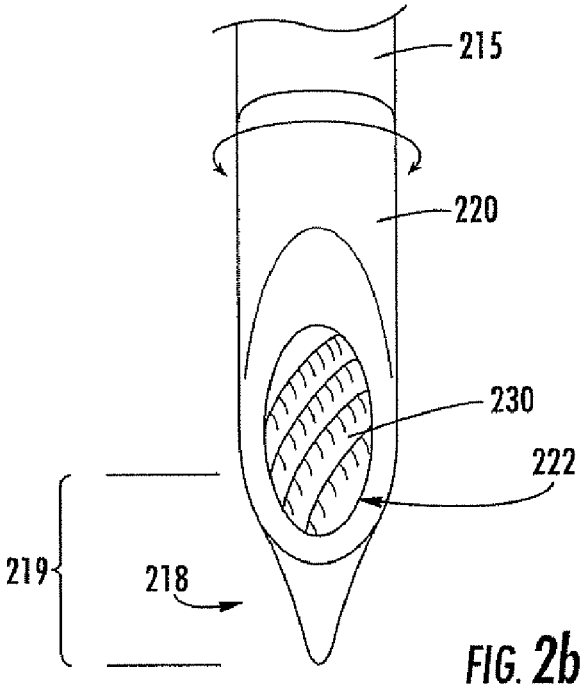

FIG. 2b is a schematic frontal view illustration of the dissecting burr of FIG. 2a. The protective hood 220 has an opening 222 exposing one portion of the burr bit 230. Generally, the superior or dorsally facing surface of the burr bit 230 is exposed while the undersurface of the burr bit 230 is protected by a protective hood 220. Again, the shape of the dissecting foot plate portion 219 of the protective hood 220 may be made in a variety of shapes as appropriate to meet the variety of dissecting action required in various spinal decompression procedures or any other bone removing procedures in which these instruments may be useful. For example, the dissecting foot plate portion 219 may be shaped like a curette or a Woodson surgical dissection tool.

Figure 2C:
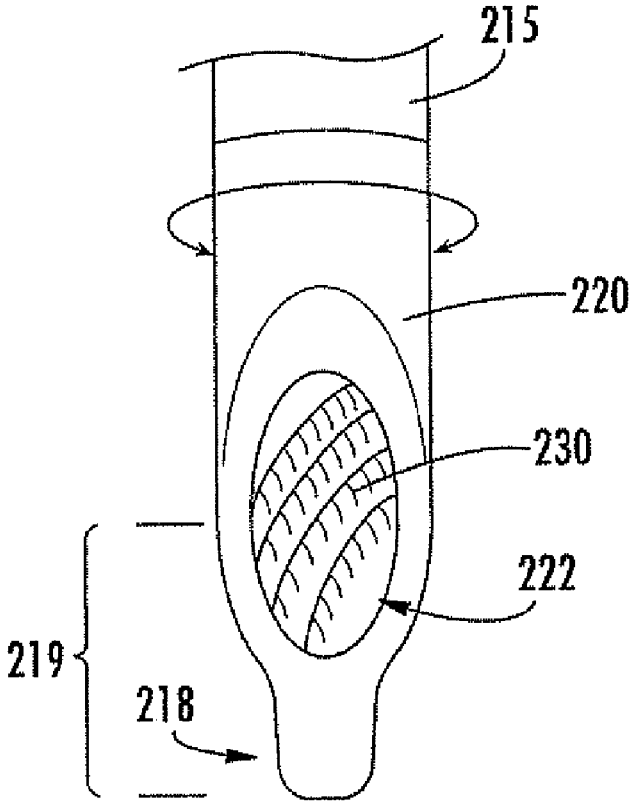
FIG. 2c is a front elevational view of the dissecting burr of FIG. 2b with an alternative shape for the dissecting foot plate according to another embodiment of the invention.

The protective hood 220 may be rotatable about the longitudinal axis 20 of the distal end of the instrument to allow the surgeon to change the direction of the burring action of the burr bit. The protective hood 220 will generally be fixed so that it does not rotate while the dissecting burr 200 is in operation (i.e. the burr bit is rotating). Adjustments in the orientation of the protective hood may be made when the instrument is turned off. In FIG. 2c, an alternative shape for the dissecting foot plate portion 219 is illustrated, which is a Woodson-type tip.

Figure 3A:
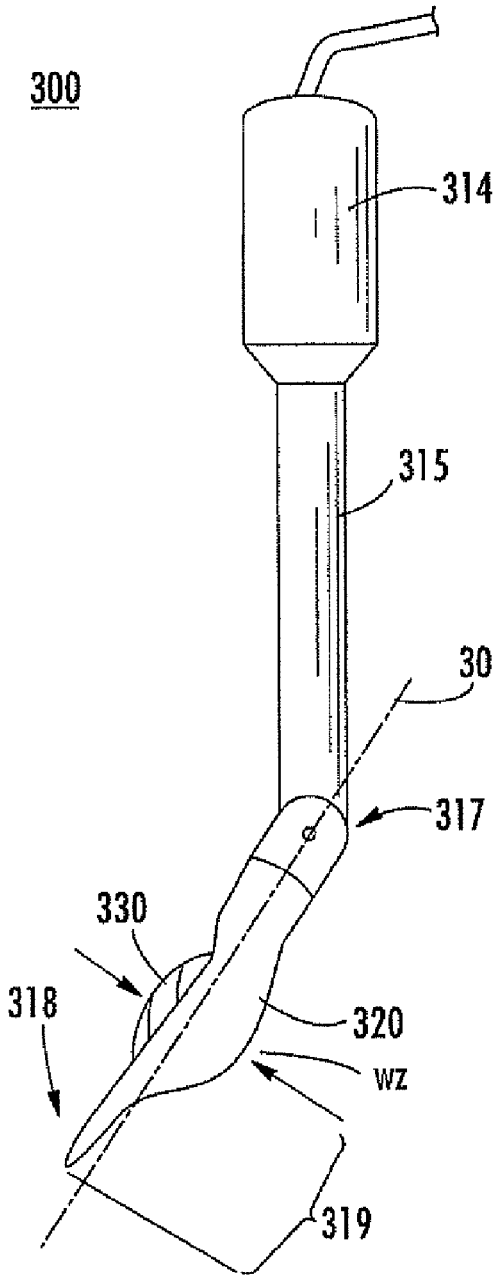
FIG. 3a is a side elevational view of a dissecting soft tissue resector according to another embodiment of the invention.
Figure 3B:
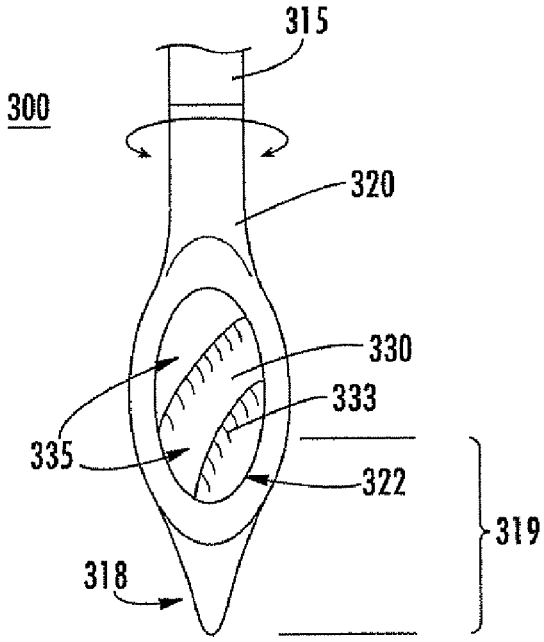
Figure 3C:
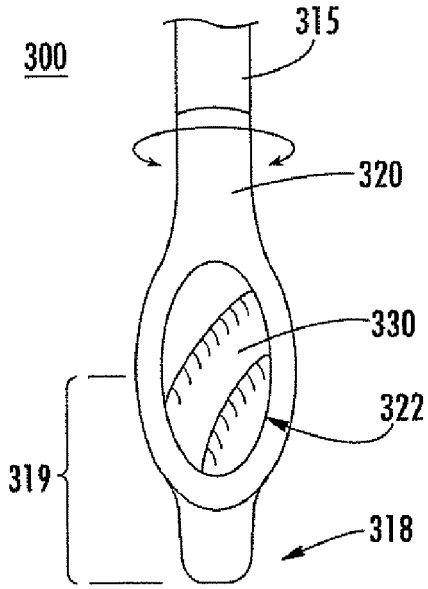
FIG. 3c is a front elevational view of the dissecting soft tissue resector of FIG. 3a having an alternative shaped dissecting foot plate according to another embodiment of the invention.

Referring to FIGS. 3a-3c, a dissecting soft tissue resector 300 according to another embodiment of the invention. The dissecting soft tissue resector 300 comprises a hand piece 314 and an outer tube 315 that functions as the shaft of the soft tissue resector 300. In this embodiment, however, the surgical tool disposed within a rotating protective hood 320 is a soft tissue resector bit 330 rather than a burr bit 130, 230. The protective hood 320 has an opening 322 exposing a portion of the soft tissue resecting bit 330. The portion of the protective hood 320 between the widest portion W2 of the protective hood and the distal tip 318 of the protective hood 320 is a dissecting foot plate portion 319, shaped to resemble a surgical dissection tool, such as a curette or a Woodson. The outer tube 315 may be angled to allow the instrument to reach into the neural foramen or other surgical sites with ease.

The protective hood 320 may be axially rotatably attached to the outer tube 315. The protective hood 320 is rotatable about a longitudinal axis 30 of the distal end 310 of the dissecting soft tissue resector 300. The opening 322 is sized and configured to expose a desired amount of the burr bit 330 appropriate for the bone removal to be performed with the instrument. This rotatable attachment allows the soft tissue resecting bit's exposed cutting portion to be repositioned to accommodate the varying geometry at the surgical site. In other words, the protective hood 320 may be axially rotated, changing the angle of attack of the soft tissue resecting bit 330. The side with the exposed soft tissue resecting bit 330 would generally be the dorsal side of the soft tissue resector 300. The soft tissue resecting bit 330 is similar to that of the meniscal debriders that are used in arthroscopic surgery.

The dissecting soft tissue resector 300 may preferably have a suction means attached to it to remove the resected tissue debris from the surgical site. Vacuum may be drawn through the outer tube 315 and to the soft tissue resecting bit 330. Preferably, the tissue resecting bit's cutting teeth 333 are spaced apart to provide sufficiently large open spaces 335 between the cutting teeth 333, allowing removal of the resected tissue debris through those open spaces by the vacuum. The soft tissue resector 300 may be configured with channel(s) or passage(s) within the instrument so that vacuum may be applied through the instrument, the open spaces between the cutting teeth 333 of the soft tissue resector bit 330 functioning as the intake opening.

The dissecting soft tissue resector 300 embodiment could also be used, with an extended kind of a Woodson-type foot plate portion 319 as shown in FIGS. 3b and 3c, to get in between compressive tissue and the nerve root that is sometimes found in the foramen that can continue to cause residual compression on the nerve, even after a dorsal bony decompression has been performed. The dissecting soft tissue resector may be used to debride annulus, ligamentum flavum, disc and or cartilage that are encroaching the nerve root in the axilla or in the foramen.

Figure 4A:
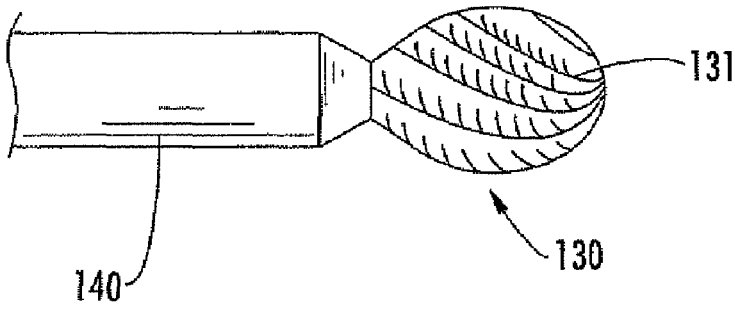
FIG. 4a is a side elevational view of an inner shaft member of the dissecting burr of FIG. 1.
Figure 4B:
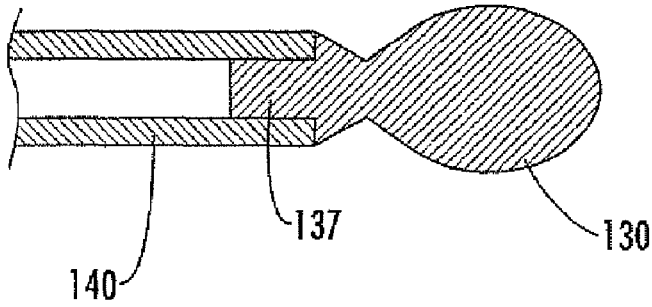

FIG. 4a is a schematic illustration of an inner shaft 140 of a dissecting burr 100 according to an embodiment of the invention with a burr bit 130 provided at its distal end. FIG. 4b is a cross-sectional schematic illustration of an inner shaft 140 and a burr bit 130 showing an example of how they may be joined together. In this example, the burr bit 130 has a base portion 137 that is inserted into the inner shaft and secured. The base portion 137 and the inner shaft 140 may be secured together by any appropriate methods such as press fitting, welding, ultrasonic welding. Alternatively the burr bit 130 may be secured to the inner shaft 140 using an adhesive. The burr bit 130 has helical cutting or abrading edges 131 on the head portion and a base portion 137 for attaching the burr bit 130 to the inner shaft 140. The inner shaft 140 is shown as a hollow tube in this example, but it may also be a flexible solid shaft made from such elastic material as Nitinol metal alloy.

The soft tissue resector 300 discussed in reference to FIG. 3 may also utilize a similar inner shaft. In that embodiment, a soft tissue resector bit 330 would be disposed at the distal end of the inner shaft. And to enable the vacuum tissue removal feature of the soft tissue resector 300, the inner shaft in this embodiment would have a tubular structure (as the inner shaft illustrated in FIG. 4b) with one or more channels therein. The soft tissue resector bit 330 may be provided with one or more channels or pathways through its base portion so that the open spaces 335 between the tissue cutting teeth 333 of the tissue resector bit 330 are communicatively connected to the one or more channels of the inner shaft. A vacuum drawn through the inner shaft of the instrument can then remove soft tissue debris from the surgical site using the open spaces 335 between the tissue cutting teeth 333 as the intake openings.

Figure 5A:
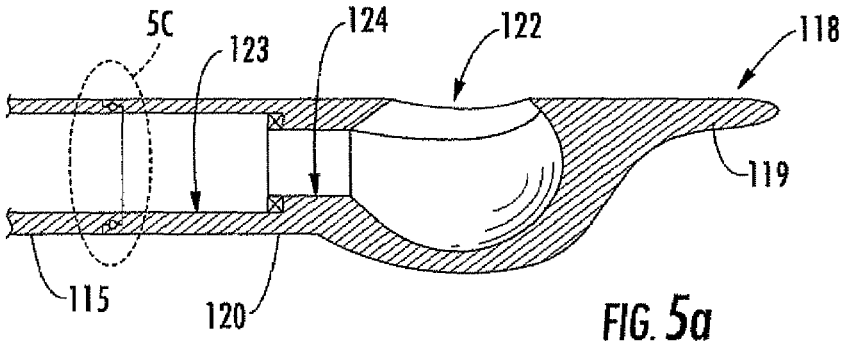
FIG. 5a is a cross-sectional schematic illustration of a protective hood of the dissecting burr of FIG. 1.
Figure 5B:
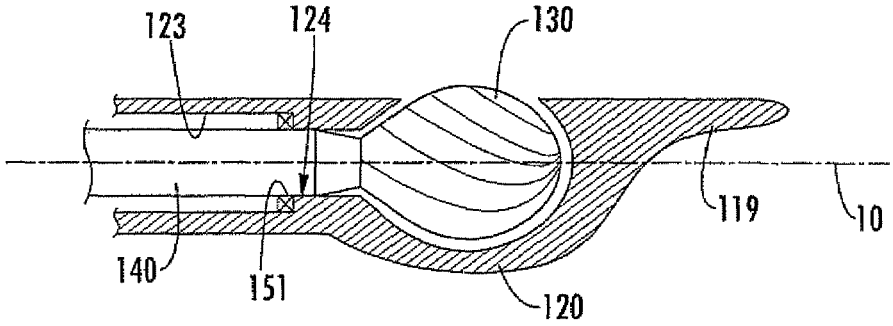
FIG. 5b is a cross-sectional schematic illustration of the protective hood of FIG. 5a with the inner shaft member of FIG. 4a disposed therein.
Figure 5C:
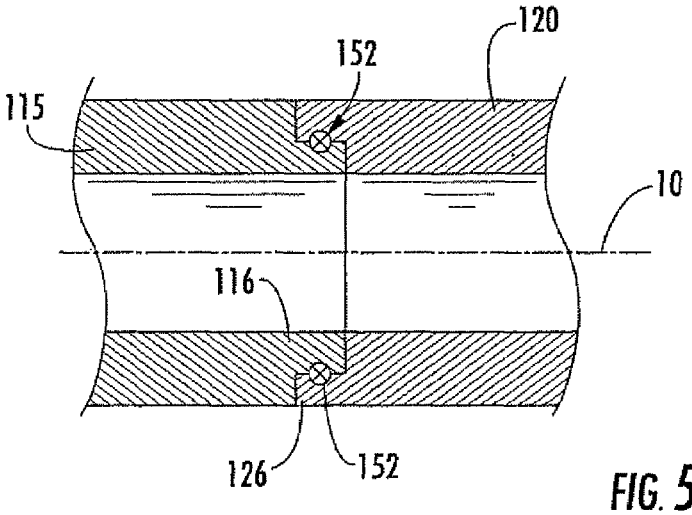

Referring to FIGS. 5a-5c, exemplary detailed views of the rotatable protective hood 120 and the burr bit 130 assembly will be discussed. FIG. 5a is a cross-sectional schematic illustration of the outer tube 115 and the rotating protective hood 120 of the dissecting burr 100 of FIG. 1. The rotating protective hood 120 is rotatably attached to the distal end of the outer tube 115. The distal end of the protective hood is the dissecting foot plate 119. The protective hood 120 has an open space 121 in which the burr bit 130 (or a soft tissue resector bit 330 in the dissecting soft tissue resector embodiment 300) attached to the inner shaft 140 may be disposed.

FIG. 5b is a schematic illustration of the protective hood 120 of FIG. 5a with the inner shaft 140 and the burr bit 130 disposed therein occupying the open space 121 inside the protective hood 120. The inner shaft 140 is disposed inside the protective hood 120 and the outer tube 115 in such manner so that the inner shaft 140 can rotate about the longitudinal axis 10. The inner surface of the outer tube 115 comprises a first inner cylindrical side wall 123 having a first diameter and a second inner cylindrical side wall 124 having a second diameter that is smaller than the first diameter. This second inner cylindrical side wall surface 124 provides a bearing means 151 that comes in contact with the inner shaft 140 allowing the inner shaft 140 to rotate about the longitudinal axis 10 with low friction. A portion of the burr bit 130 is shown exposed by the opening 122 in the protective hood 120.

FIG. 5c is a detailed schematic illustration of region B in FIG. 5a. This illustration is one example of the rotational engagement between the protective hood 120 and the outer tube 115. The proximal end of the protective hood 120 may form an outer sleeve 126 and the distal end of the outer tube may form an inner sleeve 116 that mate with one another and a suitable bearing means 152 is disposed between the mating sleeve surfaces to allow the protective hood to rotate about the longitudinal axis 10 of the distal end of the instrument. The rotatable joint between the outer tube 115 and the protective hood 120 may be formed in a variety of other configurations that are well known in the art.

The power drive mechanism for rotating the inner shaft/burr bit assembly may be any one of the known mechanisms known in the art. Many examples can be found in many conventional high speed surgical burrs, abraders, and other hand held power surgical instruments. Electrical motors or pneumatic power driven driving mechanisms commonly found in such instruments may be used to power the instrument of the invention.

As illustrated in FIGS. 1a, 2a and 3a, the outer tube 115, 215, 315 of the instruments of the invention may preferably include an angled neck portion 117, 217, 317 whose angle may be variably controlled. The power drive mechanism utilized in those embodiments would have to accommodate the angled neck. Many known flexible coupling mechanisms may be utilized here to transmit the rotational motion of the power drive mechanism, usually housed in the hand piece 114, 214, 314, to the burr bit 130, 230 or the soft tissue resector bit 330. Such flexible coupling mechanism may be, for example, multiple hinged linkages used to drive socket wrenches or helical coil flexible connectors often used with hand held drills. In another embodiment, the flexible neck portion 117, 217, 317 of the instrument may be hollow structures and a solid shaft made of elastic materials such as Nitinol metal alloy provided therethrough may connect the power drive mechanism to the tool bits 130, 230, 330 for actually driving the tool bits. One example of a flexible coupling mechanism is disclosed in U.S. Pat. No. 5,411,514 (Fucci et al.), the disclosure of which is incorporated herein by reference.

Figure 6A:
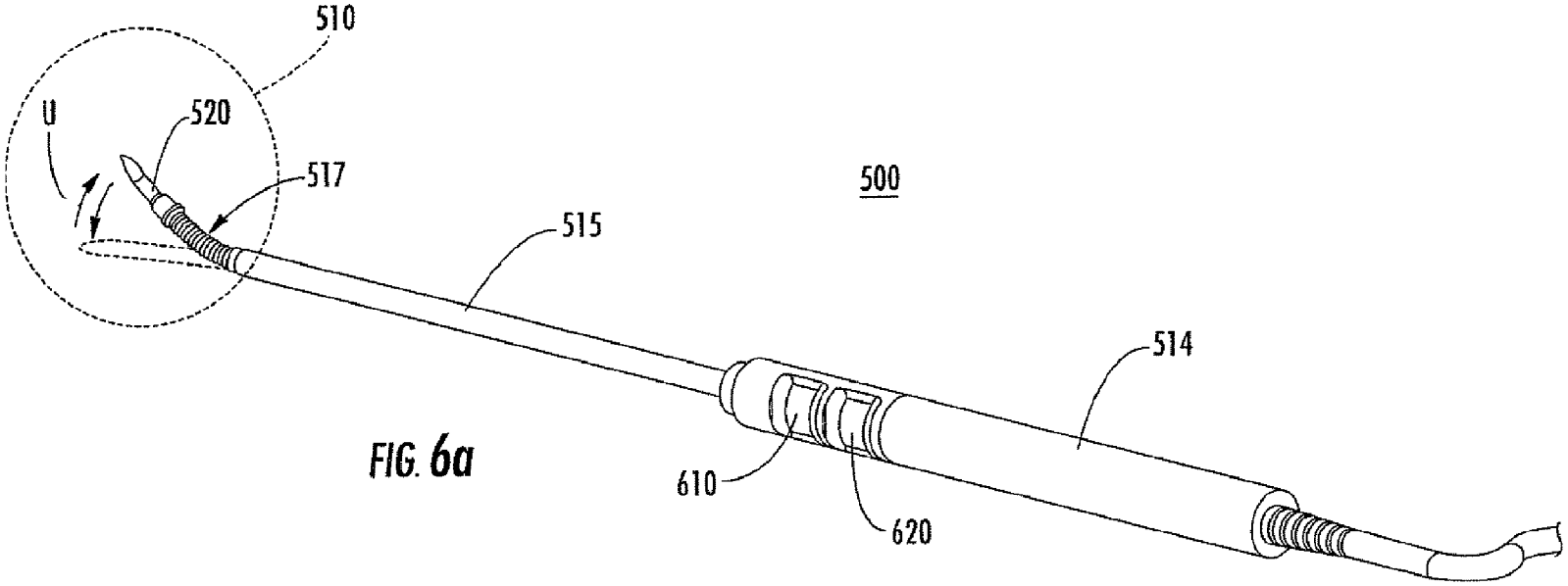
FIG. 6A is an isometric view of a dissecting burr according to an embodiment of the invention.
Figure 6B:
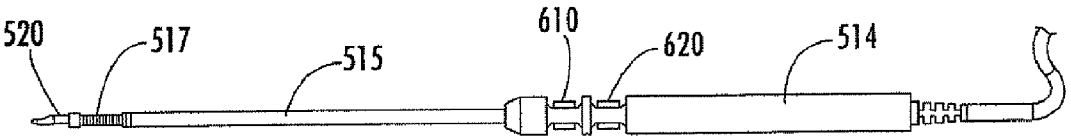
FIG. 6B is a plan view illustration of the dissecting burr of FIG. 6A.

Referring to FIGS. 6A and 6B, a dissecting burr 500 according to another embodiment of the invention is disclosed. The dissecting burr 500 is well suited for the surgical operations discussed herein. The dissecting burr 500 has an elongated shape with a dissecting burr tool at the distal end 510 and a hand piece 514 at the proximal end. Connecting the hand piece 514 and the distal end 510 of the dissecting burr 500 is a shaft portion 515. The dimensions of the shaft portion 515 and the distal end 510 of the dissecting burr 500 are such that they can be inserted through a cannula to reach the surgical site percutaneously. Provided at the distal end 510 is a burr bit partially enclosed by a protective hood 520. The protective hood 520 and the burr bit are connected to the shaft portion 515 by a flexible neck portion 517. The flexible neck portion 517 is controllably bendable in dorsal direction marked by an arrow U in FIG. 6A. The hand piece 514 may be provided with thumb wheels 610 and 620, one for controlling the rotational position of the protective hood 520 and the latter for controlling the bending angle of the flexible neck portion 517. The hand piece 514 may house a power drive mechanism for driving the burr bit. Such power drive mechanism may be any suitable source that can rotate the burr bit at high speeds, such as an electric motor or a pneumatic drive mechanism.

Figure 7A:
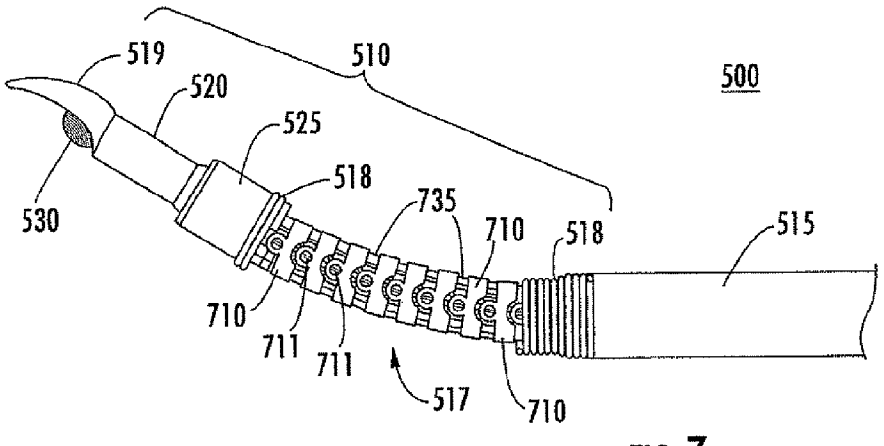
FIG. 7A is a more detailed view of the distal end of the dissecting burr of FIG. 6A.
Figure 7B:
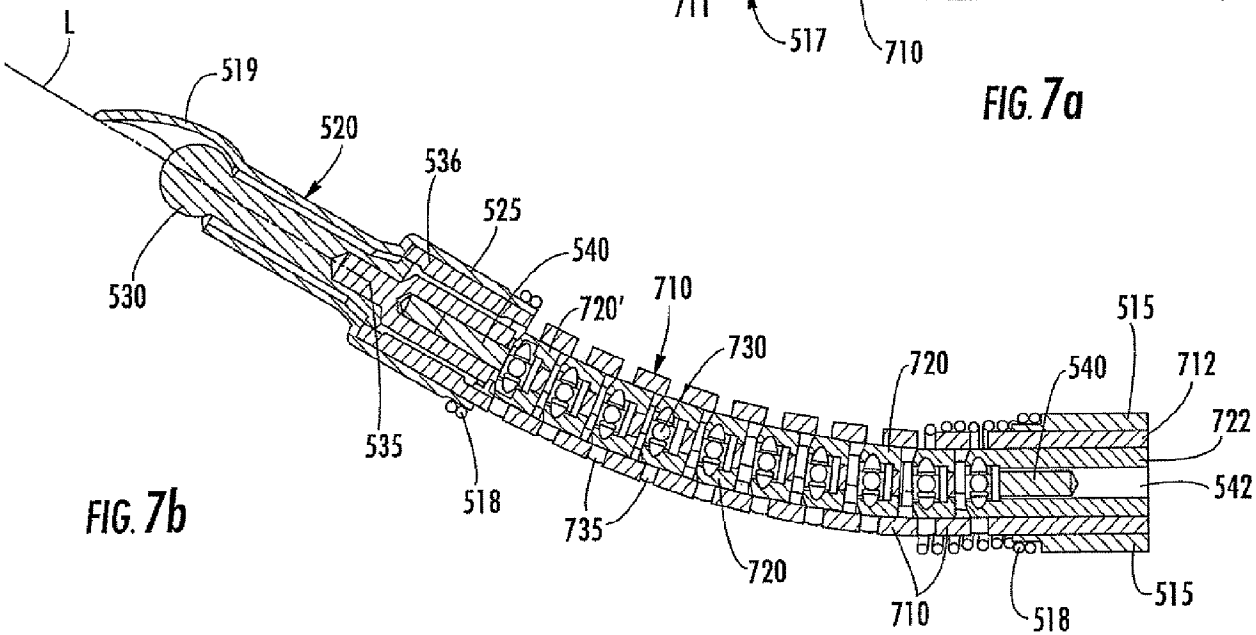
FIG. 7B is a longitudinal sectional view of the distal end of the dissecting burr of FIG. 6A.

More detailed views of the distal end 510 of the dissecting burr 500 are illustrated in side elevational view FIG. 7A and a longitudinal sectional view FIG. 7B. The protective hood 520 includes a dissecting foot plate portion 519 which partially covers the burr bit 530 leaving the burr bit 530 partially exposed in one direction for removing bone material. The protective hood 520 is rotatable about the longitudinal axis L of the burr bit 530 (which is also the longitudinal axis of the dissecting burr 500. The protective hood 520 has a base portion 525 that is connected to the tubular shaft 515 via a flexible sleeve 518, which in turn is connected to the thumb wheel 610. The user can turn or rotate the protective hood 520 by turning the thumb wheel 610 to adjust the exposure direction or the angle of attack for the burr bit 530 as desired during a surgical procedure.

As illustrated in the sectional view of FIG. 7B, the connection between the base portion 525 of the protective hood 520 and the flexible sleeve 518 may be achieved by a friction fit. In FIGS. 7A and 7B, the flexible sleeve 518, which is a helical coil type in this exemplary embodiment, is only shown at the two ends so that the internal structures of the flexible neck 517 can be better illustrated. The proximal end of the flexible sleeve 518 is affixed to the tubular shaft 515. Again, this connection may be a friction fit connection.

Figure 8:
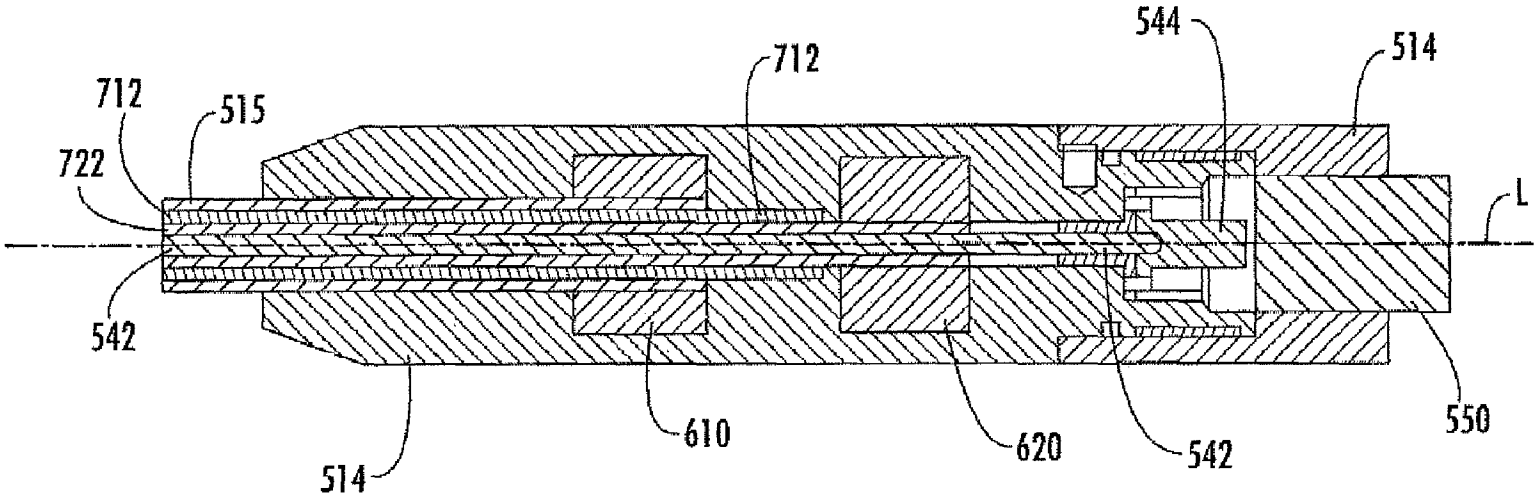
FIG. 8 is a longitudinal sectional view of the proximal end of the dissecting burr of FIG. 6A.

FIG. 8 is a sectional view of the hand piece 514 and the arrangement of the thumb wheels 610 and 620 is illustrated. The tubular shaft 515 is affixed to the first thumb wheel 610 so that turning the thumb wheel 610 also turns the tubular shaft 515 which, in turn, turns the flexible sleeve 518, which then turns the protective hood 520. The flexible sleeve 518 may be a helical coil type as illustrated in FIGS. 7A and 7B. The thumb wheel 610, the tubular shaft 515, the flexible sleeve 518, and the protective hood 520, all share a common rotational axis, which is the longitudinal axis L of the dissecting burr 500. The thumb wheel 610 may be provided with an appropriate mechanism (not shown) to lock the thumb wheel 610 from rotating in order to lock the orientation of the protective hood 520 after being adjusted. A variety of locking mechanism may be used for such purpose and it would be obvious to one of ordinary skill in the art to employ such mechanisms.

Nested inside the tubular shaft 515 is a first inner tube 712 (FIGS. 7B and 7C). The first inner tube 712 at the proximal end extends into the hand piece 514 and is friction fitted or affixed by other appropriate means to the hand piece 514 to prevent it from turning about the longitudinal axis L. At its distal end, the first inner tube 712 is connected to a series of outer links 710 which extend through the flexible sleeve 518 and hingeably connects to a burr drive spindle housing 536 (FIG. 7B). As illustrated in FIG. 7A, the outer links 710 are hingeably linked to each other by a hinge 711. Because the first inner tube 712 is non-rotatably affixed to the hand piece 514, the outer links 710 also are not rotatable about the longitudinal axis L. The linkage formed by the outer links 710 are, however, bendable in one direction, the dorsal direction U, marked in FIG. 6A. This is because the outer links 710 are lined up so that the rotational axis M (FIG. 9A) through their hinges 711 are orthogonal to the dorsal direction U.

As illustrated in FIG. 7B, nested inside the first inner tube 712 is a second inner tube 722. The second inner tube 722 at its proximal end extends into the hand piece 514 and it is friction fitted or affixed by other appropriate means to the second thumb wheel 620. At its distal end, the second inner tube 722 is connected to a series of inner links 720 which extend through the outer links 710, with the last inner link 720' stopping at the end of the flexible neck portion 517. Thus, the inner links 720 are not connected to anything at the distal end. The inner links 720 are hingeably linked to each other by hinge pins 737 (FIG. 9B). As will be further discussed below in more detail, turning the second thumb wheel 620 rotates the inner links 720 and causes the assembly formed by the outer links 710 to bend up or down in the dorsal direction U.

As shown in FIG. 7B, nested inside the second inner tube 722 is a drive shaft 542. The drive shaft 542 may be a rigid shaft and at its proximal end it extends into the hand piece 514 and is affixed to a drive linkage 544 which connects the drive shaft 542 to a power drive unit 550. The power drive unit 550 may be an electric motor, a pneumatic drive unit, or any other suitable mechanism that can turn the drive shaft 542 at desired speeds. The drive shaft 542 at its distal end is affixed to a second drive shaft 540 that is flexible. The second drive shaft 540 may be made of strong and elastic material such as Nitinol alloy. The second drive shaft 540 extends through the inner links 710 and at the distal end is affixed to a burr drive spindle 535. The burr drive spindle 535 is, in turn, connected to a burr bit 530. Alternatively, the second drive shaft 540 may be directly connected to the burr bit 530 without the intermediate structure such as the spindle 535. Alternatively, the flexible second drive shaft 540 may extend all the way to the drive linkage 544 in the hand piece 514 so that a single piece drive shaft extends from the drive linkage 544 to the burr bit 530 or the burr bit spindle 535. The interface between the spindle 535 and the spindle housing 536 is provided with a suitable lubricant or bearing arrangement so that the spindle 535 may rotate with minimal frictional interference. Similarly, the interface between the spindle housing 536 and the base portion 525 of the protective hood 520 is also provided with a suitable lubricant or bearing arrangement.

Figure 9D:
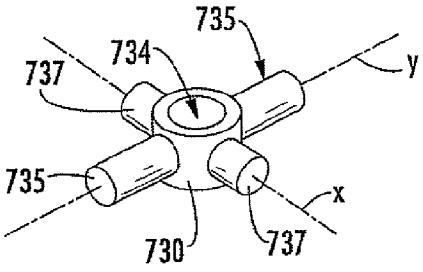
FIGS. 9A-9F are various illustrations of the flexible neck portion of the distal end of the dissecting burr of FIG. 6A.
Figure 9C:
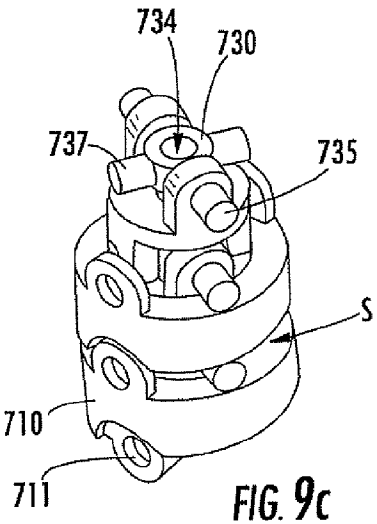
Figure 9B:
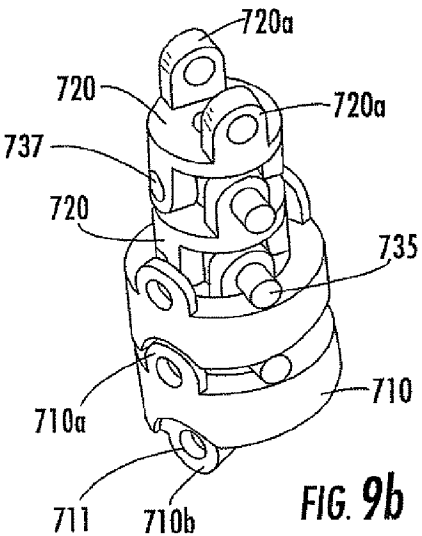
Figure 9A:
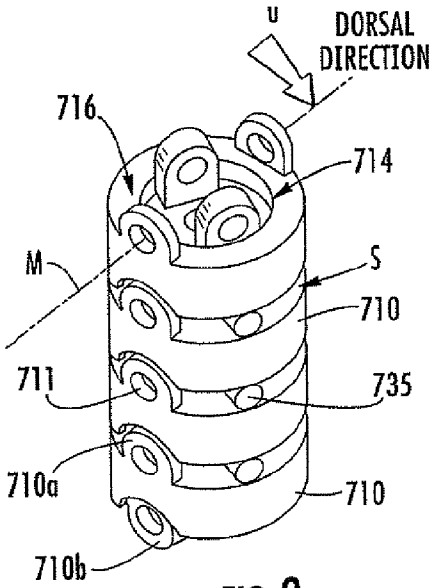
Figure 9F:
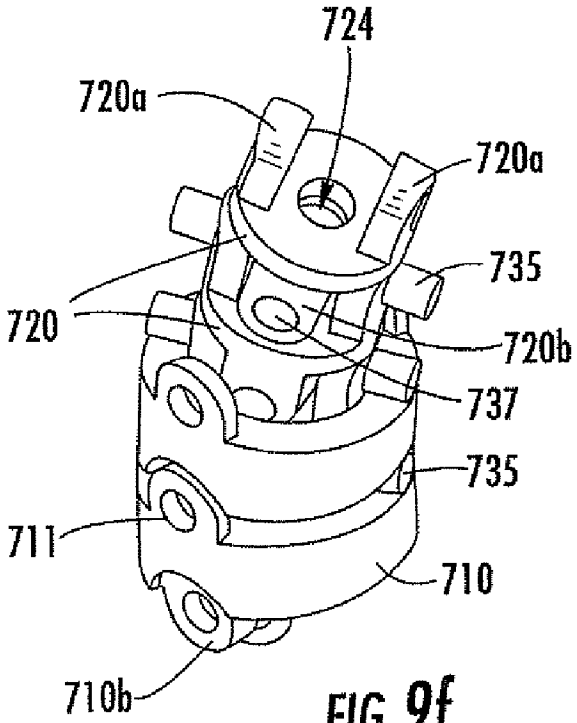

Referring to FIGS. 9A-9F and 10A-10C, the controllably bending mechanism of the flexible neck portion 517 achieved by the outer links 710 and the inner links 720 in this exemplary dissecting burr 500 will be described. As mentioned above, the outer links 710 form a non-rotating assembly that is bendable in one direction. The bending enabled by the hinges 711 connecting each outer links. Each of the outer links 710 have center hole 714 so that the outer links 710 form a bendable tube-like structure within which sits the structure formed by the inner links 720. The inner links are hingeably connected to each other by the hinge pins 737. Each of the inner links 720 also have center hole 724 (FIG. 9F). Each inner link 720 has a pair of lower ears 720b and a pair of upper ears 720a, transversely oriented from the lower ears 720b. The hingeable links between the inner links 720 are formed by a cross-shaped pin subassembly 730 (FIG. 9D). The pin subassembly 730 comprises a pair of short hinge pins 737. The hinge pins 737 mate with the lower ears 720b of the inner links 720 thereby hingeably connecting them. The pin subassembly 730 also comprises a pair of long camming pins 735 whose longitudinal axis Y is oriented transverse to the longitudinal axis X of the short hinge pins 737. The pin subassembly 730 is assembled in between two inner links 720 so that the camming pins 735 extend through the upper ears 720a of the inner links 720 and into camming spaces S formed between the outer links 710. The pin subassembly 730 is provided with center hole 734 that aligns with the center hole 724 of the inner links 724.

Figure 9E:
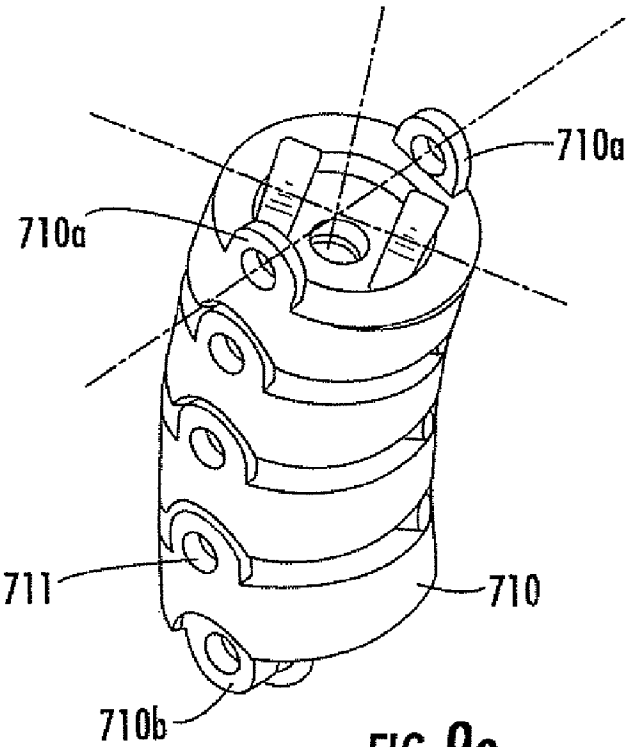
Figure 10A:
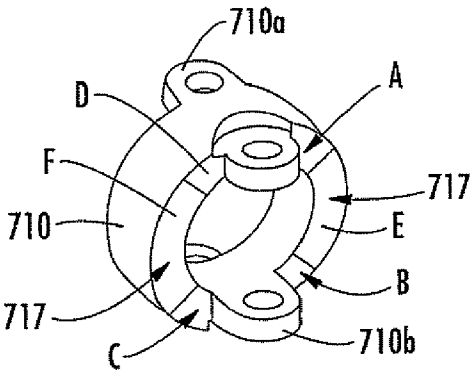
FIGS. 10A-10C are detailed illustrations relating to how the flexible neck portion bends.
Figure 10C:
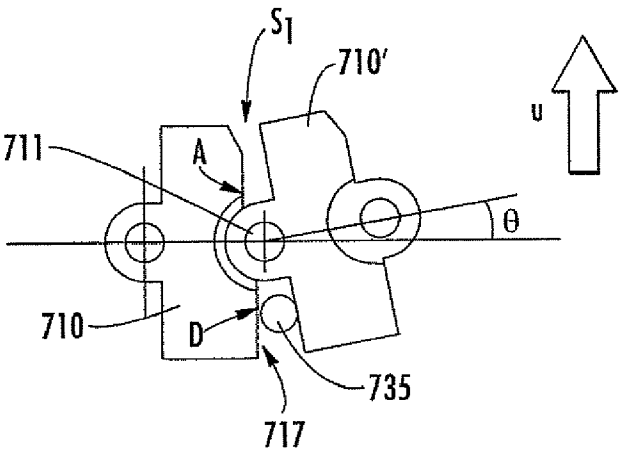
Figure 10B:
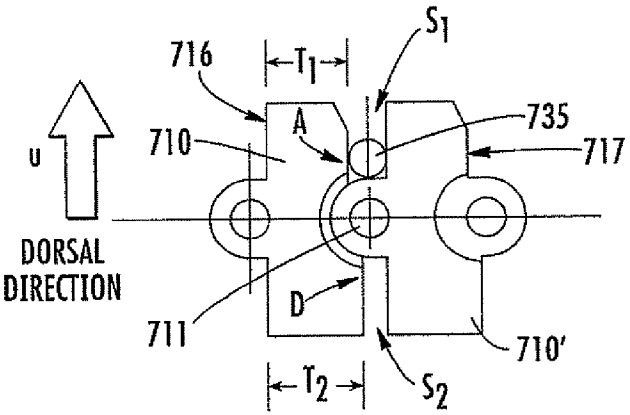

Referring to FIG. 10A, each outer link 710 has a first surface 716 that is flat and a second surface 717 that is specifically contoured. The second surface 717 forms the camming surface for the camming pins 735 which extends into the camming space S formed between the outer links 710. The camming surface 717 is contoured so that as the camming pins 735 rotates in the camming space S, the two adjacent outer links 710 are forced to bend about the hinge 711 in the dorsal direction U and back to the straight configuration. The camming surface 717 of the outer link 710 is contoured to have at least 6 regions marked as A, B, C, D, E, and F in FIG. 10A. FIG. 10B illustrates the configuration where two adjacent outer links 710 and 710' are in a straight arrangement. Thus, this represents the configuration where the flexible neck 517 of the dissecting burr 500 is, in turn, straight. The inner links 720 have been rotated so that one end of their camming pin 735 is positioned in the camming space S. The camming pin 735 is at the region A of the camming surface 717. The opposite end (not shown) of the camming pin 735 is on the opposite side at the region C of the camming surface 717. This position of the camming pin 735 will be referred to as the A-C position. Illustrated in FIG. 10C is the configuration in which the outer links 710 and 710' are at their maximum bending angle θ. The camming pin 735 is now at the regions D and B of the camming surface 717. This position of the camming pin 735 will be referred to as the B-D position. As illustrated in FIGS. 10B and 10C, the thickness T1 of the outer link 710 at camming region A is thinner than the thickness T2 of the outer link 710 at the camming region D. Correspondingly, the camming space S1 is larger than the camming space S2. Thus, as the camming pin 735 transitions from the A-C position to the B-D position, the camming pin 735 pushes the outer links 710 and 710' apart at the S2 side and causing the outer links to pivot relative to each other about the hinge 711. By rotating the inner links 720 and moving the camming pin 735 back to the A-C position, the camming pin 735 now pushes the outer links 710 and 710' apart at the S1 side pivoting the outer links back to the straight configuration shown in FIG. 10B. FIG. 9A illustrates the outer link assembly in a position where the camming pins 735 are somewhat close to the A-C position and FIG. 9E illustrates the outer link assembly in a position where the camming pins 735 are somewhat closer to the B-D position. It should be noted that the maximum range for the amount of bending that may be manipulated for a given dissecting burr 500 can be varied as desired by changing the contour of the camming surface 717 of the outer links and the number of outer links used to form the flexible neck portion 517.

Figure 11A:
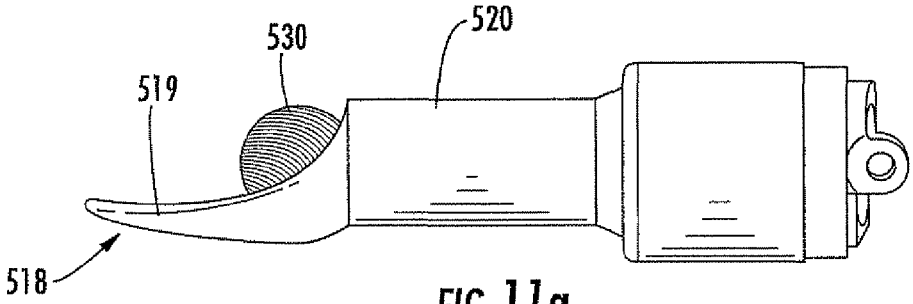
FIGS. 11A-11D are detailed illustrations of a burr hood according to an embodiment of the invention.
Figure 11B:
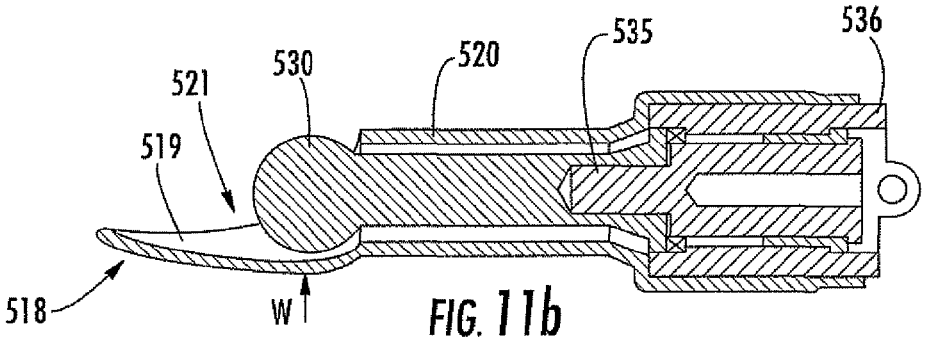
Figure 11C:
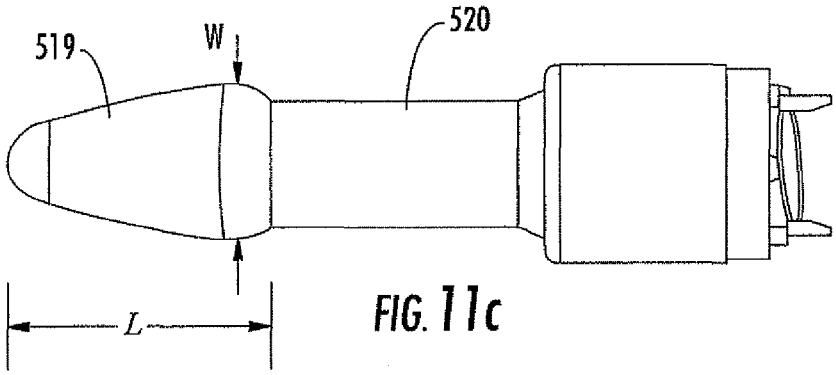
Figure 11D:
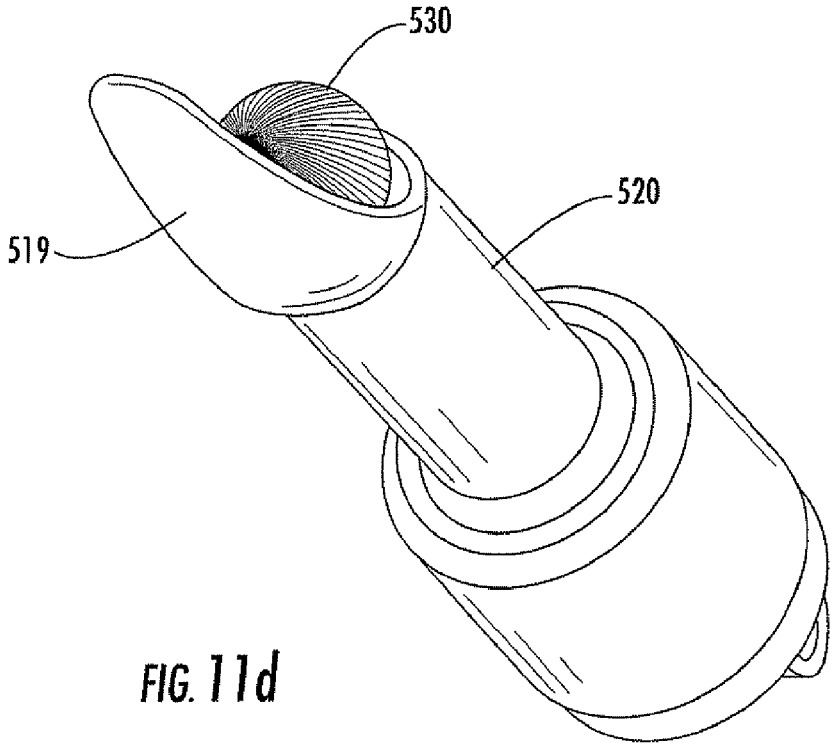

FIGS. 11A-11D are more detailed illustrations of the protective hood 520 of the dissecting burr 500 of FIG. 6A. The side view, FIG. 11A, and the sectional view FIG. 11B, show that the dissecting foot plate portion 519 of the protective hood 520 partially enclose the burr bit 530. The dissecting foot plate portion 519 in this exemplary embodiment is similarly shaped to the Woodson dissecting tool, with the dissecting foot plate 519 extending from the widest portion W of the protective hood 520 towards the distal tip 518 beyond the burr bit 530 providing a space 521. The burr bit end of the dissecting burr 500 can be inserted into a surgical site, such as the interval between the nerve root and the encroaching bone in a neural foramen without the need for a separate dissecting tool and without the risk of damaging the surrounding soft tissue such as the nerve root. The surgeon would rotate the protective hood 520 so that the foot plate portion 519 is positioned to be between the burr bit 530 and the nerve root as the surgeon inserts the burr bit end of the instrument into the surgical site.

Figure 12A:
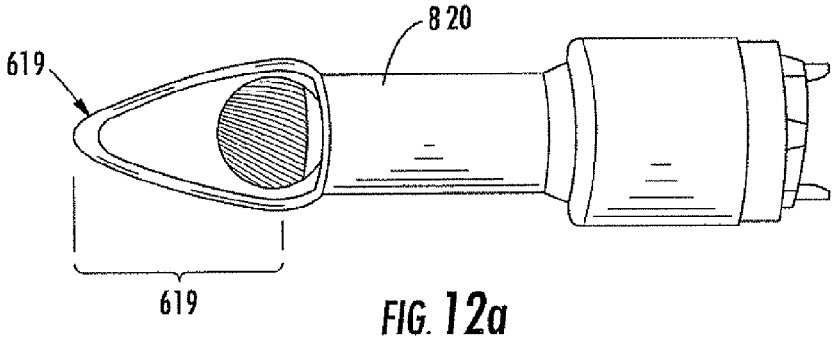
FIGS. 12A-12C and 13A-13C are detailed illustrations of a burr hood according to another embodiment of the invention.
Figure 12B:
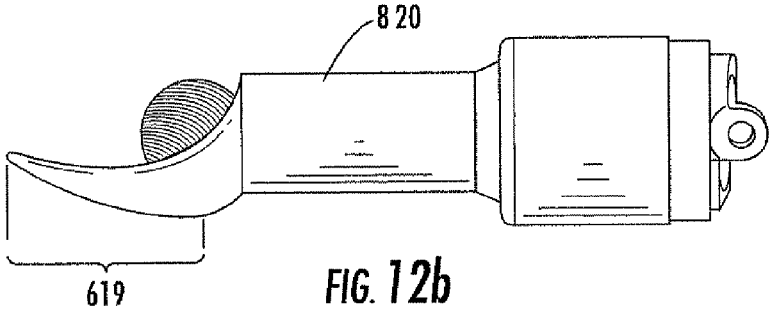
Figure 12C:
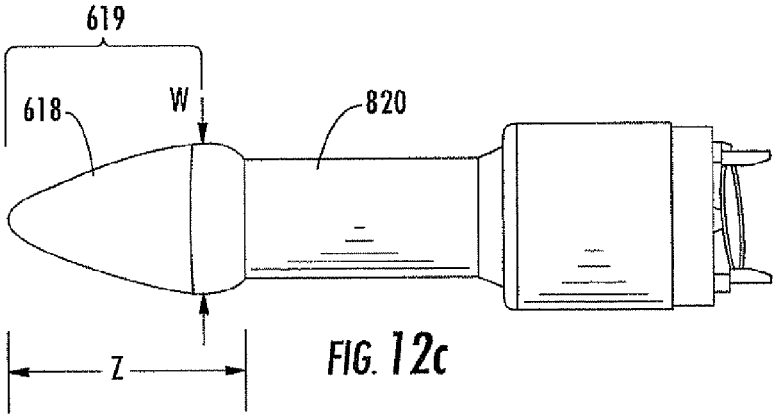

FIGS. 12A-12C are illustrations of another protective hood 820 for the dissecting burr 500 having another dissecting foot plate 619 having a pointed or tapered distal tip 618 according to another embodiment. As mentioned above, the dissecting foot plate portion may be configured and adapted to have many different shapes that are appropriate for a particular application but all for providing a dissecting function.

Figure 13A:
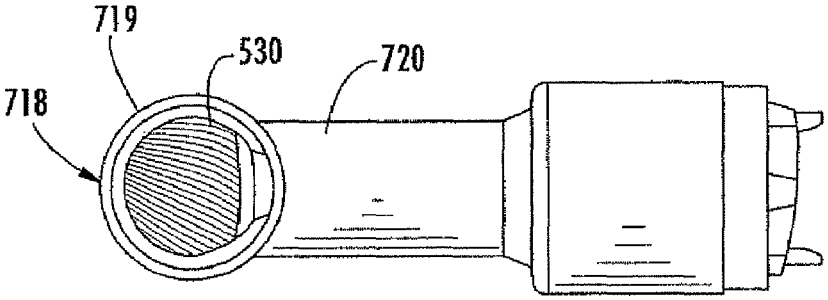
Figure 13B:
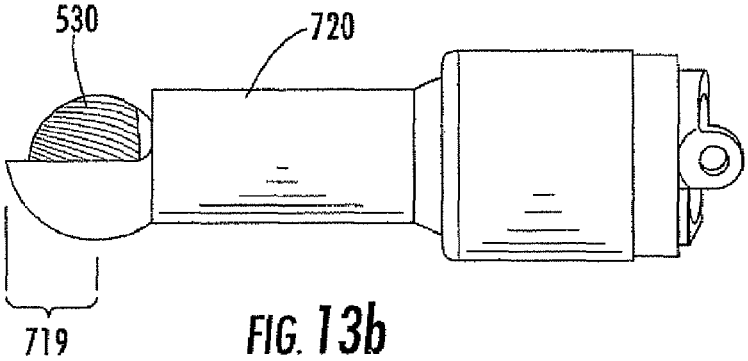
Figure 13C:
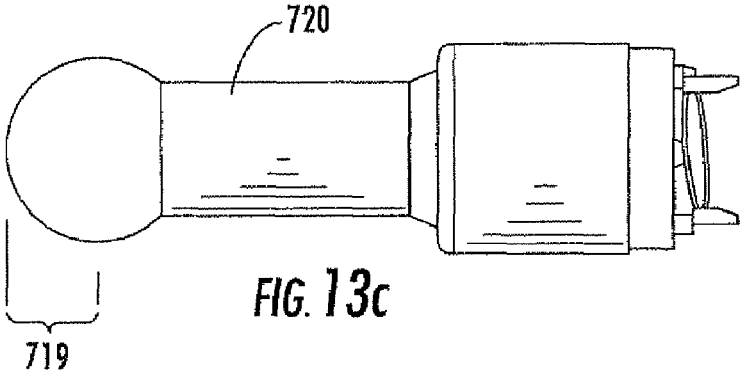

FIGS. 13A-13C are illustrations of another protective hood 720 for the dissecting burr 500 having a curette-type dissecting foot plate 719 according to another embodiment. The curette-type dissecting foot plate 719 of this embodiment does not extend out beyond the burr bit 530 as much as the Woodson-type dissecting foot plates 519, 619. The curette-type dissecting foot plate 719 has a short curved shape.

The dissecting foot plate portions 519, 619 and 719 have length Z of about 7.5 mm and a diameter at the widest portion W of about 4.5 mm. For surgical applications involving lumbar decompression surgical procedures such as lumbar laminectomy and foraminotomy, the dissecting foot plate portion may have a length of about 1 mm (currette-like tip) to about 8 mm (Woodson-like tip). The diameter of the foot plate portion at the widest portion W may be about 2 mm to 10 mm depending on the burr bit size.

With current minimally invasive lumbar decompression techniques, a retracting cannula is placed at the interspace percutaneously via sequential dilators. This technique works well for disc herniations where the pathology can be accessed at the interspace. The draw back to this technique with lumbar decompressions is that the ipsilateral lateral recess and foramen are extremely difficult to decompress because the line of sight afforded by the cannula does not allow the surgeon to get a direct view into the recess or the foramen on the ipsilateral side. Therefore, some surgeons have modified the technique and taken the cannula and directed it contralaterally to afford a view at the contralateral lateral recess and foramen. The drawback of this technique is that you disrupt the interspinous ligament and reaching across the dural space risks tearing the dura. In addition, attempting a foraminal decompression and lateral recess decompression in this fashion is technically extremely demanding because of the limited view and the limited maneuverability afforded by the small working diameter of the cannula. The cannulas typically have a diameter of about 2 centimeters. This could be made even more technically demanding in a patient with an extremely stenotic lateral recess and foramen.

The spinal instruments of the invention provides many advantages over the conventional instruments in performing minimally invasive lumbar decompressions. Lateral recess decompression can be performed on the ipsilateral side and also a foraminotomy can be performed on the ipsilateral side. Therefore, the interspinal ligaments can be preserved and all that is necessary to complete a full decompression is making a midline incision to bring the cannula to one side of the spinous process and the interspinous ligaments to perform one side of the lateral decompression. The cannula is then pulled out and reenter the spine on the contralateral side, through the same incision, on the other side of the spinous process and interspinous ligament and perform the contralateral lumbar lateral recess and foraminal decompression. In this way the interspinous ligament and the spinous processes are preserved and that posterior tension band is not violated. In order to perform the lateral recess decompression, an endoscope must be placed, similar to the conventional scopes that can be attached to the retracting cannula, however, it needs to be angled at a 60-70 degree angle so that it has a view directly into the lateral recess and the foramen.

Because the high speed dissecting burr 100, 200 of the invention does not require a large amount of force or a large arc of motion to perform a bone resection, the lateral recess and foraminal decompression can be performed safely and accurately in minimally invasive setting. Because of the precision of bone resection allowed by the high speed dissecting burr 100, 200 of the invention, the actual amount of bone that is resected can be minimized just to the bone that is encroaching on to the nerve root or the dural elements in the lateral recess. Thus, the amount of bony resection can be minimized to what is necessary to adequately decompress the neural elements. This maximally preserves the facet joints, thereby minimizing post-decompression instability.

A number of benefits are realized by the use of the surgical instruments of the invention described herein. For example, by performing the bone and ligament sparing lumbar decompression, the lamina can be preserved. The ligamentum just needs to be removed at the interspace, which often is the main source of compression, and the bone encroaching the lateral recess from facet hypertrophy and the foraminal stenosis can be adequately decompressed using the high speed dissecting burr and dissecting spinal soft tissue resector.

Since the amount of facet resection can be minimized and the posterior spinal ligaments preserved by using the high speed dissecting burr of the invention, it may be possible to clinically avoid fusion in patients with mild instability and mild spondylolisthesis because most of the spinal stability and the spinal integrity can be preserved. However, in patients where fusions are deemed to be warranted, the decompressions can be performed in a minimally invasive setting and since the lamina are preserved, one can attempt an interlaminar spinal fusion. Also, because the intertransverse plane is not dissected, there is no lateral soft tissue stripping that needs to be performed lateral to the facets and the intertransverse plane, therefore the morbidity to the patient is significantly minimized and the patient's postoperative recovery will be enhanced. Thus, there is no additional soft tissue dissection that is required than is done with a normal laminectomy.

By using the surgical instruments of the invention, preservation of bone and interspinal ligaments can be maximized during spinal decompression procedures. And since a good portion of the spinal stability is maintained by preserving the bone and interspinal ligaments, the overall patient satisfaction will be much improved in the strictly lumbar decompression patients. Furthermore, by combining the decompression performed with the instruments of the invention with a minimally invasive interlaminar fusion, possibly supplemented with minimally invasive pedicle screw system, the spinal segment fusion can be performed with a higher union rate and faster recovery times since the intertransverse muscle plane can be spared.

The surgical instruments of the invention also have applications in other areas of the spine. In the cervical spine, for example, the dissecting burr may be used for posterior foraminotomies. In such procedure, the dorsal surface of the spinal nerve root is first located and the dissecting burr is inserted overlying the nerve root under microscopic visualization and a foraminotomy may be performed that maximally preserves the cervical facet joint.

The dissecting burr of the invention may also enhance anterior cervical surgery, for example, during anterior cervical corpectomies. The width of the corpectomy trough is limited by concerns of the vertebral artery being violated at the lateral margin. Often the lateral decompression is incomplete because of fear of violating the vertebral artery, which can be catastrophic. With the use of the dissecting burr of the invention, the dissecting portion of the burr can be inserted into the interval between the vertebral artery and the lateral margins of the anterior cervical vertebral body and resect the lateral bony edge. This would allow the surgeon to perform a complete cervical corpectomy rather than a partial one.

Also, for anterior cervical disc work, the dissecting burr of the invention can be used to perform anterior cervical foraminotomies and osteophytectomies by inserting the burr into the interval between the lateral margin of the uncus and the vertebral artery by protecting the vertebral artery and allowing complete resection of the uncovertebral joint and thereby decompressing the foramina laterally and allowing preservation of the disc space medially and avoiding cervical fusion.

According to an aspect of the invention, the various embodiments of the instruments described herein may be configured so that irrigation fluid may be delivered to the surgical site via the instrument. There are many examples of surgical instruments known in the art having such irrigating feature that may be incorporated into the instruments of the invention. Example of burring or similar type of instruments with irrigation feature are described in, for example, U.S. Pat. No. 5,782,795 (Bays); U.S. Pat. No. 6,068,641 (Varsseveld); and U.S. Pat. No. 6,503,263 (Adams), the disclosures of which are incorporated herein by reference. In both the dissecting burr and the dissecting soft tissue resector embodiments of the invention, channels or pathways may be provided within the instrument for supplying irrigation fluid to the surgical site. Irrigation fluid would serve to assist in removal of tissue debris from the surgical site as well as cooling the surgical tool tip, the burr bits 130, 230 and the soft tissue resector bit 330, during the surgical procedure. Keeping the tool tip cool prevents damaging bone, nerve, or surrounding tissues during the surgical procedure. The irrigation can also help to collect the bone or other tissue debris for removal from the surgical site.

The instruments of the invention may also be configured for removing the tissue debris from the surgical site by vacuum. As discussed in reference to the soft tissue resector embodiment of the invention, the surgical tool tip may be configured to have open spaces between the cutting or abrading teeth sufficiently large for removal of tissue debris. The protective hood 120, 220, 320 or the outer tube 115, 215, 315 may also be configured with openings that may serve as intake ports for removing tissue debris by suction from in and around the surgical site. Many examples of surgical burrs and other abraders having such tissue removal features are known in the industry.

While the foregoing invention has been described with reference to the above embodiments, various modifications and changes can be made without departing from the spirit of the invention. Accordingly, all such modifications and changes are considered to be within the scope of the appended claims.

What is claimed is:

1. A surgical instrument comprising:

a hand piece having a distal end and a proximal end;

a shaft portion extending from the distal end of the hand piece and having a distal end and a proximal end;

a drive shaft disposed for rotation within the shaft portion, the drive shaft having a distal end and a proximal end thereof;

a surgical tool bit connected to the distal end of the drive shaft;

a protective hood including a dissecting foot plate portion connected to the distal end of the shaft portion, wherein the surgical tool bit resides within the protective hood, partially exposed, and the protective hood is rotatable relative to the surgical tool bit exposing a different portion of the surgical tool bit; [and]

a rotatable member provided in the hand piece, said rotatable member operably connected to the proximal end of the shaft portion and manipulation of the rotatable member controls the rotation of the protective hood relative to the hand piece and the drive shaft via the shaft portion*; and*

*a flexible neck portion connecting the protective hood to the distal end of the shaft portion, wherein the drive shaft comprises a flexible drive shaft portion at the distal end thereof and extending through the flexible neck portion to connect to the surgical tool bit,*

*wherein the flexible neck portion is communicatingly connected to the hand piece and the flexible neck portion's flexing motion is actuated and controlled from the hand piece*.

2. The surgical instrument of claim 1, wherein the dissecting foot plate portion has a length of about 1 to 8 mm.

[3. The surgical instrument of claim 1, further comprising a flexible neck portion connecting the protective hood to the distal end of the shaft portion, wherein the drive shaft comprises a flexible drive shaft portion at the distal end thereof and extending through the flexible neck portion to connect to the surgical tool bit.]

[4. The surgical instrument of claim 3, wherein the flexible neck portion is communicatingly connected to the hand piece and the flexible neck portion's flexing motion is actuated and controlled from the hand piece.]

5. The surgical instrument of claim [3] *1*, wherein the flexible drive shaft portion is made of Nitinol alloy.

6. The surgical instrument of claim 1, wherein the shaft portion is a rigid member.

7. The surgical instrument of claim 1, wherein the surgical tool bit is a bone removing bit.

8. The surgical instrument of claim 1, wherein the surgical tool bit is a soft tissue resecting bit.

9. The surgical instrument of claim 1, wherein the rotatable member is a thumb wheel.

10. A surgical instrument comprising:

a hand piece having a distal end and a proximal end;

a power drive mechanism provided within the hand piece;

a shaft portion extending from the distal end of the hand piece and having a distal end and a proximal end;

a drive shaft disposed for rotation within the shaft portion, the drive shaft having a distal end and a proximal end thereof, wherein the proximal end is connected to the power drive mechanism;

a surgical tool bit connected to the distal end of the drive shaft;

a protective hood including a dissecting foot plate portion attached to the distal end of the shaft portion, wherein the surgical tool bit resides within the protective hood, partially exposed, and the protective hood is rotatable relative to the surgical tool bit exposing a different portion of the surgical tool bit; and a rotatable member provided in the hand piece, said rotatable member operably connected to the proximal end of the shaft portion and manipulation of the rotatable member controls the rotation of the protective hood relative to the hand piece and the drive shaft via the shaft portion*; and*

*a flexible neck portion connecting the protective hood to the distal end of the shaft portion, wherein the drive shaft comprises a flexible drive shaft portion at the distal end thereof and extending through the flexible neck portion to connect to the surgical tool bit,*

*wherein the flexible neck portion is communicatingly connected to the hand piece and the flexible neck portion's flexing motion is actuated and controlled from the hand piece*.

[11. The surgical instrument of claim 10, further comprising a flexible neck portion connecting the protective hood to the distal end of the shaft portion, wherein the drive shaft comprises a flexible drive shaft portion at the distal end thereof and extending through the flexible neck portion to connect to the surgical tool bit.]

[12. The surgical instrument of claim 11, wherein the flexible neck portion is communicatingly connected to the hand piece and the flexible neck portion's flexing motion is actuated and controlled from the hand piece.]

13. The surgical instrument of claim [11] *10*, wherein the flexible drive shaft portion is made of Nitinol alloy.

14. The surgical instrument of claim 10, wherein the shaft portion is a rigid member.

15. The surgical instrument of claim 10, wherein the surgical tool bit is a bone removing bit.

16. The surgical instrument of claim 10, wherein the surgical tool bit is a soft tissue resecting bit.

17. The surgical instrument of claim 10, wherein the rotatable member is a thumb wheel.

* * * * *